US006617488B1

(12) United States Patent
Springer et al.

(10) Patent No.: US 6,617,488 B1
(45) Date of Patent: *Sep. 9, 2003

(54) METHOD AND APPARATUS FOR INDICATING THE CONDITIONS IN AN ABSORBENT ARTICLE

(75) Inventors: John S. Springer, San Anselmo, CA (US); Jerry Lee Tappa, Livermore, CA (US); Bruce George Pound, Menlo Park, CA (US)

(73) Assignee: Indicator Technologies, Inc., San Anselmo, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/479,955

(22) Filed: Jan. 10, 2000

Related U.S. Application Data

(63) Continuation-in-part of application No. 08/949,965, filed on Oct. 14, 1997, now abandoned.

(51) Int. Cl.[7] ................. A61F 13/15; A61F 13/20
(52) U.S. Cl. .................. 604/361; 604/360
(58) Field of Search ................ 604/359–362; 602/41–43, 48; 422/84.04; 324/438

(56) References Cited

U.S. PATENT DOCUMENTS

| | | | | |
|---|---|---|---|---|
| 2,886,771 A | * | 5/1959 | Vincent | 324/438 |
| 3,004,895 A | * | 10/1961 | Schwartz | 604/361 |
| 3,648,159 A | * | 3/1972 | Stansell et al. | 324/30 |
| 3,731,685 A | | 5/1973 | Eidus | |
| 3,903,259 A | | 9/1975 | Hart | |

(List continued on next page.)

FOREIGN PATENT DOCUMENTS

| | | |
|---|---|---|
| CA | 678754 | 1/1964 |
| DE | 3810473 | 3/1988 |
| DE | 2031104 | 12/1997 |
| FR | 2680678 | 3/1993 |
| GB | 2250121 | 5/1992 |

OTHER PUBLICATIONS

Stedman's Medical Dictionary, 26th edition. pp. 1892–1893 Definition of urine. 1995.*
RC Wands, Chapter Forty–One, Alkaline Materials, *Patty's Industrial Hygiene and Toxicology* $3^{rd}$. Revised Ed.(1981), pp. 3045–3070.
WS Ferguson et al., *Journal of Occupational Medicine* vol. 19 No. 5, 1977, pp. 319–326.
RW Berg et al., Pediatric Dermatology, Feb. 1986 "Etiologic Factors in Diaper Dermatitis: The Role of Urine," pp. 102–106.
JA Davis et al., Pediatric Dermatology, 1989 "Comparison of Disposable Diapers with Fluff Absorbent and Fluff Plus Absorbent Polymers: Effects on Skin Hydration, Skin pH, and Diaper Dermatitis," pp.102–108.
JJ Leyden et al., Archives of Dermatology, Dec. 1977, 113, 1678–1680 "Urinary Ammonia and Ammonia–Producing Microorganisma in Infants With and Without Diaper Dermatitis," pp. 1678–1680.

(List continued on next page.)

*Primary Examiner*—Weilun Lo
*Assistant Examiner*—Joseph F. Weiss, Jr.
(74) *Attorney, Agent, or Firm*—Kenyon & Kenyon

(57) ABSTRACT

A method and apparatus for gauging the levels of pH in the interiors of articles such as diapers, incontinence garments, pads, catamenial products, bedding, and would dressings are disclosed. This method and apparatus include sensing devices and relay systems for displaying the pH on the outside of the articles that provide visual and/or audible warnings that toxic levels are approaching and that it is time to remove and replace the article.

13 Claims, 7 Drawing Sheets

U.S. PATENT DOCUMENTS

| | | | |
|---|---|---|---|
| 3,964,486 A | 6/1976 | Blaney | |
| 4,029,597 A | 6/1977 | Nesius et al. | |
| 4,063,452 A | 12/1977 | Bradshaw | |
| 4,090,013 A | 5/1978 | Ganslaw et al. | |
| 4,185,100 A | 1/1980 | Rovee et al. | |
| 4,231,370 A | 11/1980 | Mroz et al. | |
| 4,260,950 A * | 4/1981 | Hadden et al. | 324/438 |
| 4,273,786 A | 6/1981 | Kraskin | |
| 4,360,518 A | 11/1982 | Rovee et al. | |
| 4,447,775 A * | 5/1984 | Breuker et al. | 324/438 |
| 4,507,121 A | 3/1985 | Leung | |
| 4,556,560 A | 12/1985 | Buckingham | |
| 4,583,546 A | 4/1986 | Garde | |
| 4,657,537 A | 4/1987 | Zimmerer | |
| 4,683,318 A | 7/1987 | Deffeyes et al. | |
| 4,685,909 A | 8/1987 | Berg et al. | |
| 4,744,374 A | 5/1988 | Deffeyes | |
| 4,795,482 A | 1/1989 | Gioffre et al. | |
| 4,822,456 A | 4/1989 | Bryan | |
| 4,826,497 A | 5/1989 | Marcus et al. | |
| 4,834,733 A | 5/1989 | Huntoon et al. | |
| 4,842,593 A | 6/1989 | Jordan et al. | |
| 4,868,024 A | 9/1989 | Cross et al. | |
| 4,887,602 A | 12/1989 | O'Leary | |
| 4,895,567 A | 1/1990 | Colon et al. | 604/361 |
| 4,931,051 A | 6/1990 | Castello | |
| 4,940,945 A * | 7/1990 | Littlejohn et al. | 324/438 |
| 4,985,023 A | 1/1991 | Blank et al. | |
| 5,013,335 A | 5/1991 | Marcus | |
| 5,035,691 A | 7/1991 | Zimmel et al. | |
| 5,061,487 A | 10/1991 | Blank et al. | |
| 5,080,902 A | 1/1992 | Allenmark et al. | |
| 5,089,548 A | 2/1992 | Zimmel et al. | |
| 5,110,593 A | 5/1992 | Benford | |
| 5,114,418 A | 5/1992 | Levy | |
| 5,120,548 A | 6/1992 | McClelland et al. | |
| 5,137,525 A | 8/1992 | Glassman | |
| 5,137,526 A | 8/1992 | Coates | |
| 5,161,686 A | 11/1992 | Weber et al. | |
| 5,181,905 A | 1/1993 | Flam | |
| 5,194,261 A | 3/1993 | Pichierri | |
| 5,217,444 A | 6/1993 | Schoenfeld | |
| 5,218,304 A * | 6/1993 | Kinlen et al. | 324/438 |
| 5,229,105 A | 7/1993 | Wilmsmann | |
| 5,230,702 A | 7/1993 | Lindsay et al. | |
| 5,261,896 A | 11/1993 | Conway et al. | |
| 5,268,852 A * | 12/1993 | Forsythe et al. | 364/482 |
| 5,306,487 A | 4/1994 | Karapasha et al. | |
| 5,312,379 A | 5/1994 | Rahe | |
| 5,354,289 A | 10/1994 | Mitchell et al. | |
| H1376 H | 11/1994 | Osborne, III et al. | |
| 5,360,422 A | 11/1994 | Brownlee et al. | |
| 5,362,488 A | 11/1994 | Sibley et al. | |
| 5,399,343 A | 3/1995 | Smith | |
| 5,409,476 A | 4/1995 | Coates | |
| 5,417,977 A | 5/1995 | Honeycutt | |
| 5,436,007 A | 7/1995 | Hartung et al. | |
| 5,466,229 A | 11/1995 | Elson | |
| 5,468,236 A * | 11/1995 | Everhart et al. | 604/361 |
| 5,509,915 A | 4/1996 | Hanson et al. | |
| 5,536,783 A | 7/1996 | Olstein et al. | |
| 5,558,655 A | 9/1996 | Jezzi et al. | |
| 5,595,754 A | 1/1997 | Ito et al. | |
| 5,643,588 A | 7/1997 | Roe et al. | |
| 5,709,222 A | 1/1998 | Davallou | |
| 5,747,666 A * | 5/1998 | Willis | 73/1.02 |
| 5,760,694 A | 6/1998 | Nissim et al. | |
| 5,788,687 A | 8/1998 | Batich et al. | |
| 5,808,554 A | 9/1998 | Shuminov | |
| 5,817,076 A | 10/1998 | Fard | |
| 5,823,953 A | 10/1998 | Roskin et al. | |
| 5,827,913 A | 10/1998 | Baetzold et al. | |
| 5,840,584 A | 11/1998 | Waldenburg | |
| 5,843,575 A | 12/1998 | Wang et al. | |
| 5,849,405 A | 12/1998 | Wang et al. | |
| 5,868,723 A * | 2/1999 | Al-Sabah | 604/361 |
| 5,900,258 A | 5/1999 | Engler | |
| 5,902,296 A | 5/1999 | Fluyeras | |
| 5,902,669 A | 5/1999 | Steinhardt et al. | |
| 5,903,222 A | 5/1999 | Kawarizadeh et al. | |
| 5,925,572 A * | 7/1999 | Byrne et al. | 436/163 |
| 6,149,636 A * | 11/2000 | Roe et al. | 604/361 |
| 6,186,991 B1 * | 2/2001 | Roe et al. | 604/361 |
| 6,186,992 B1 | 2/2001 | Roe et al. | |
| 6,203,496 B1 * | 3/2001 | Gael et al. | 600/362 |
| 6,258,027 B1 | 7/2001 | Sternby | |
| 6,372,951 B1 * | 4/2002 | Ter-Ovanesyan et al. | 604/361 |
| 6,384,296 B1 * | 5/2002 | Roe et al. | 604/361 |
| 6,433,244 B1 * | 8/2002 | Roe et al. | 604/361 |

OTHER PUBLICATIONS

RW Berg et al., Advances in Dermatology, Aug. 1988 "Etiology and Pathophysiology of Diaper Dermatitis," pp. 75–98.

RL Campbell et al., Pediatric Dermatology, Dec. 1987 "Effects of Diaper Types on Diaper Dermatitis Associated with Diarrhea and Antibiotic Use in Children in Day–Care Centers," pp. 83–87.

JW Tyler, Medical Hypostheses, Jan. 1985, pp. 61–64.

JS Kemp et al., Journal of Pediatrics, Jun. 1993 "Unintentional suffocation by rebreathing: A death scene and physiologic investigation of a possible cause of sudden infant death," pp. 874–880.

HC Kinney et al., Science, Sep. 1995 "Decreased Muscarinic Receptor Binding in the Arcuate Nucleus in Sudden Infant Death Syndrome," pp. 1446–1450.

NM Sayers et al., *Journal of Clinical Pathology*, Oct. 1995 "Lethal synergy between toxins of staphylococci and enterobacteria: implications for sudden infant death syndrome," pp. 929–932.

IB Masters et al., *Archives of Diseases of Childhood*, Dec. 1994 "Surfactant abnormalities in ALTE and SIDS," pp. 501–505.

DV Hatton et al., *Archives of Environmental Health*, Mar. 1979 "Collagen Breakdown and Ammonia Inhalation," pp. 83–87.

JS Kemp et al., Pediatric Research, Jul. 1994 "Physical Properties of Bedding That May Increase Risk of Sudden Infant Death Syndrome in Prone–Sleeping Infants," pp. 7–11.

G Malcolm et al., *Journal of Pediatrics and Child Health*, Feb. 1994, "Carbon dioxide concentrations in the environment of sleeping infants," pp. 45–49.

LG Close et al., *Archives of Otolaryngal Medicine*, Mar. 1980 "Acute and Chronic Effects of Ammonia Burns of the Respiratory Tract," pp. 151–158.

VS Kalandarov et al., Space Biology and Aerospace Medicine, 18(3) 1984 "Effect of High Ammonia Content in Pressure Chamber Atmosphere on Human Adrenocortical System Function".

AM Glasgow et al., *American Journal of Disease of Childhood*, Feb. 1975 Exchange Transfusion to Remove Ammonia,' pp. 159–160.

Handbook of Chemistry and Physics, $55^{th}$ Ed., CRC Press, Cleveland, Ohio 1974, p. D–115–116.

RL Campbell et al., *J. Am. Acad. Dermatol,* 1987, 17, "Clinical Studies with Disposable Diapers Containing Absorbent Gelling Materials: Evaluation of Effects on Infant Skin Condition," pp. 978–987.

AT Lane et a.l, *Am. J. Dis. Childhood,* 1990, 144, "Evaluations of Diapers Containing Absorbent Gelling Material with Conventional Disposable Diapers in Newborn Infants," pp. 315–318.

News Release "Pampers Introduces . . . Prevent Diaper Rash" 2 pages.

T Agner, *Acid. Derm. Venereol Suppl.,* 1992, Supp. 177, "An Experimental Study of Irritant Effects of Urea in Different Vehicles," pp. 44–46.

* cited by examiner pH KINETIC VARIABILITY IN DIAPERS

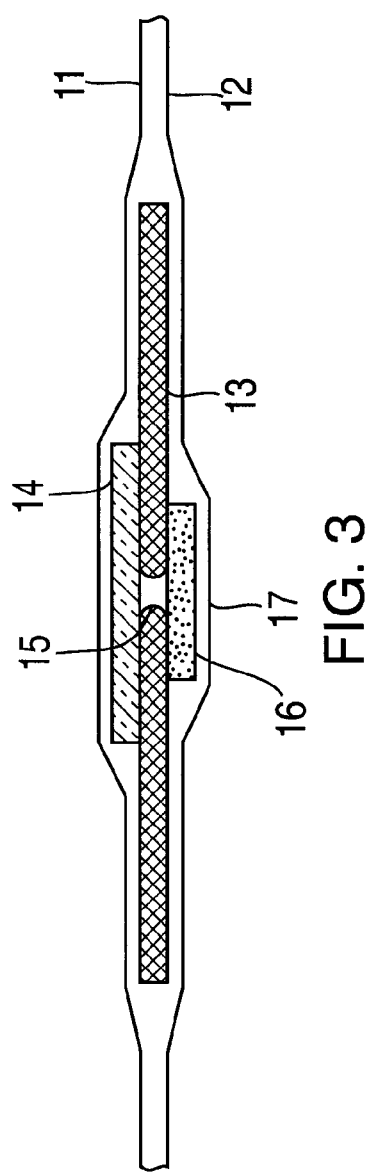
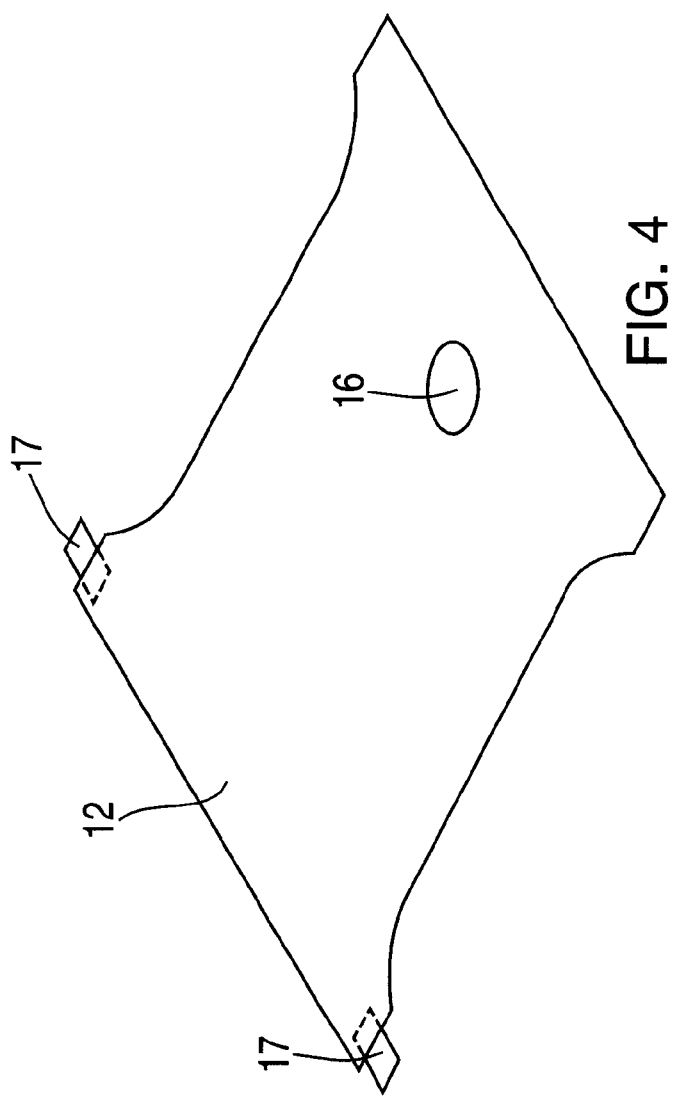

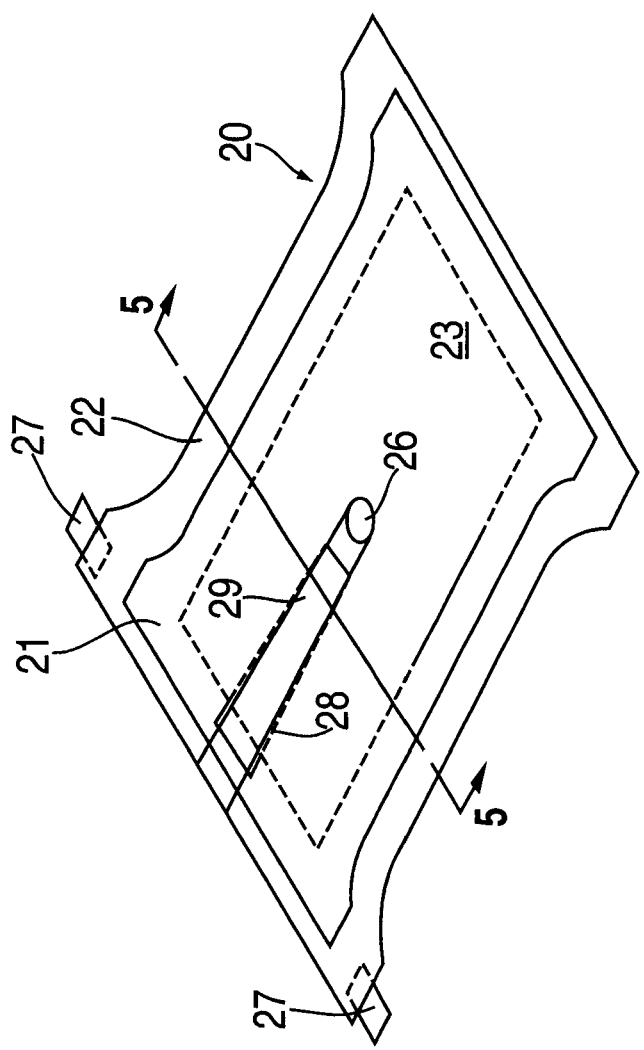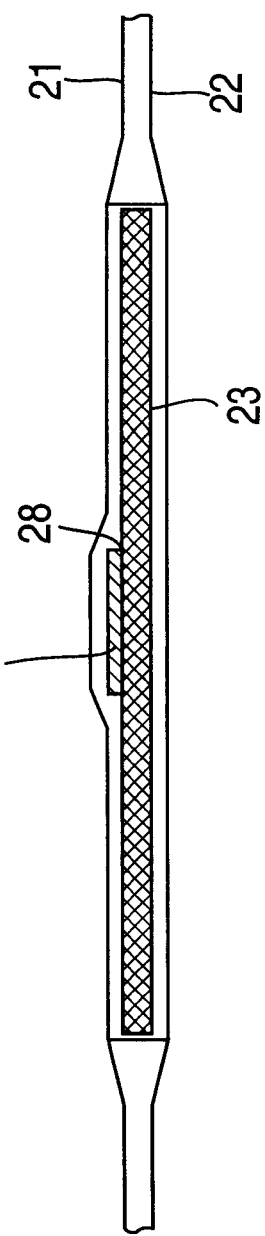

METHOD AND APPARATUS FOR INDICATING THE CONDITIONS IN AN ABSORBENT ARTICLE

CROSS-REFERENCE TO RELATED APPLICATIONS

This application is a continuation-in-part of application Ser. No. 08/949,965, filed Oct. 14, 1997 now abandoned.

FIELD OF THE INVENTION

The present invention relates to a novel method and apparatus for measuring the pH in diapers and other such absorbent articles, and more particularly to a method and apparatus for signaling incipient pathogenic and pathological conditions in the environment of the article.

BACKGROUND OF THE INVENTION

With the increase of mothers employed away from home, and the increase in adult diaper-wearers, there is strong demand for diapers and other disposable garments that can be worn for longer periods. To meet this demand, superabsorbent and dry-feel materials have been developed. Most diaper products contain materials that can absorb many times their weight in urine. They are normally worn for more than four hours and frequently for eight hours or longer. Superabsorbent diapers that feature leakage barriers have also been developed, as well as new ammonia odor control technologies.

Prior to these new technologies, it was commonly accepted that the human olfactory system was the ideal monitor for sensing the onset of toxic ammonia concentrations. But the new diaper technologies have caused such major changes in the pH levels and in the volumes, concentrations, and migration of ammonia gas in diapers, that olfactory sensing is no longer reliable. In addition, since new diaper technologies channel urine away from the interior surface, leaving a dry feel, the sense of touch can no longer inform the caregiver that the diaper may contain a substantial amount of urine.

Onset toxicity of anhydrous ammonia as a caustic agent occurs at concentrations of 20 to 35 ppm. See NIOSH *Criteria for Recommended Standard Exposure to Ammonia* #74-136; Proctor et al., *Chemical Hazards of the Workplace* (2ed. 1988). The human odor threshold for ammonia gas ranges from 5 to 50 ppm, although regular exposure to low levels builds olfactory tolerance for higher levels. In the new diapers, ammonia gas concentrations can quickly reach 50 ppm, but the characteristic ammonia odor is, to some degree, contained within the diaper barriers and/or masked by new technologies designed specifically for that purpose. Thus, there is now a need for other methods to warn caregivers of ammonia build-up.

Within the diapered-area temperature and pH are higher than normal, friction is greater and microbes multiply faster than in non-diapered areas. The skin is wetter than normal, non-diapered skin, and wet skin is more vulnerable to damage than dry skin. The combination of these factors causes or contributes to diaper area pathologies.

Diaper-area temperature, microbiological load, and pH are greater in disposables than in cloth diapers. The higher pH in disposables triggers diaper dermatitis, the most prevalent of diaper area diseases. This disease is caused by the actions of proteolytic enzymes, which metabolize the skin and subcutaneous tissue.

Ammonia dermatitis, another diaper area disease, normally occurs only after healthy skin has been continuously exposed to ammonia at greater than 10,000 ppm for more than 15 minutes. See Procter et al., *Chemical Hazards of the Workplace* (2nd ed. 1988). In a diapered area where the epidermis has already been compromised, ammonia exacerbates the pre-existing condition.

Urine entering a diaper is sterile and has a pH of about 6.2. Ammonia gas escapes the urine. At this point, the entire diaper-area pH begins to rise. It will continue to rise, at an increasing rate, until the diaper is changed or the urea exhausted.

Ammonia is small, polymorphous, and highly soluble in water, and is highly mobile. Ammonia is also soluble in lipids and can migrate across many cell membranes. As the skin pH increases through the 7.0 to 9.0 range, the alkalinity overcomes the lactic acid buffering capacity of the epidermis and inflicts caustic burning, causing ammonia dermatitis. In addition, ammonia gas is also a suffocant that can cause life-threatening stenosis or, if inspired suddenly, gastrointestinal reflex/reflux. Furthermore, ammonia is a sedative that, if inspired gradually over time, can impair an infant's central nervous system and medullary and adrenocortical functions.

A major concern regarding long-lasting, leak-proof diapers is that the urine permeable membrane enclosing the absorbent matrix often leaks or ruptures, most often during the time period after urine pH has reached about 8.5. During this period, free ammonia continuously builds up within the diaper, and fluid pressures will continue to build within the absorbent core. The pressures of the fluids and gases against the diaper's liquid permeable topsheet matrix membrane are said to have reached the breakthrough point when an external mechanical pressure of 0.5 psi forces fluids and gases to reverse-permeate the diaper's liquid permeable topsheet and contact skin. Such mechanical pressures can include the wearer rolling over or the diaper being forcefully pressured by unyielding objects, such as crib siding, a car seat or a wheelchair. When the pressures within the sheath increase past the breakthrough point, the topsheet may leak or rupture, releasing toxic dissolved and free ammonia and carbon dioxide. The matter released may contain a significant biomass inoculum of rapidly multiplying bacteria including Proteus supp. This highly toxic mix contacts skin, and, if present, feces and pre-existing lesions.

U.S. Pat. No. 4,231,370 to C. Mroz et al. relates to a disposable diaper having a wetness indicator that is a pH-change/color-change stripe visible from the exterior of the diaper. The indicator comprises an absorbent color-change material (bromophenol blue) in a matrix of highly flexible latex adhesive. This indicator only indicates wetness; it does not measure or indicate pH changes or ammonia concentrations.

U.K. Patent No. 2 250 121 to Lee relates to a disposable diaper wherein moisture closes a circuit, activating an audible alarm signaling that the diaper is wet.

French Patent No. 2 680 678 to Ly relates to the use of a moisture sensor linked to a transmitter in a diaper that sends a signal to a receiver kept by parents.

The prior art that notifies caregivers of wetness in a diaper has some utility since wet skin is more vulnerable to damage than dry skin, but short-term wetness, in itself, is not damaging. Diaper-area wetness becomes dangerous to healthy skin only in conjunction with other irritants. Prior art wetness indicators that rely on pH measurement function in a binary mode; that is, they indicate simply whether an article is wet or dry, with no indication of the degree of wetness. A pH indication based solely on the presence of urine is useful, but does not indicate whether the urine is decomposing and therefore shifting to a more alkaline pH, which will lead to an unsafe environment. While the prior art attempts to solve the urine-ammonia problem at its source, until now there has been no method for warning the caregiver that the harmful conditions are imminent.

SUMMARY OF THE INVENTION

The present invention provides a method and apparatus for warning the caregiver of a diaper-wearer when the pH concentration within the diaper approaches a degree of toxicity that can cause or exacerbate damage to the wearer's skin and other membranes.

With the foregoing and other objects, advantages and features of the invention that will become hereinafter apparent, the nature of the invention may be more clearly understood by reference to the following detailed description of the invention, the appended claims and to the several views illustrated in the drawings.

BRIEF DESCRIPTION OF THE DRAWINGS

FIG. 3 is a cross-sectional view taken along line 3—3 of FIG. 2.

FIG. 4 is a perspective view of the exterior of a diaper incorporating a chemically reactive indicator means.

FIG. 5 is a perspective view of the interior of a diaper incorporating a chemically reactive indicator means.

FIG. 6 is a cross-sectional view taken along line 6—6 of FIG. 5.

DETAILED DESCRIPTION OF THE INVENTION

Figure 1:
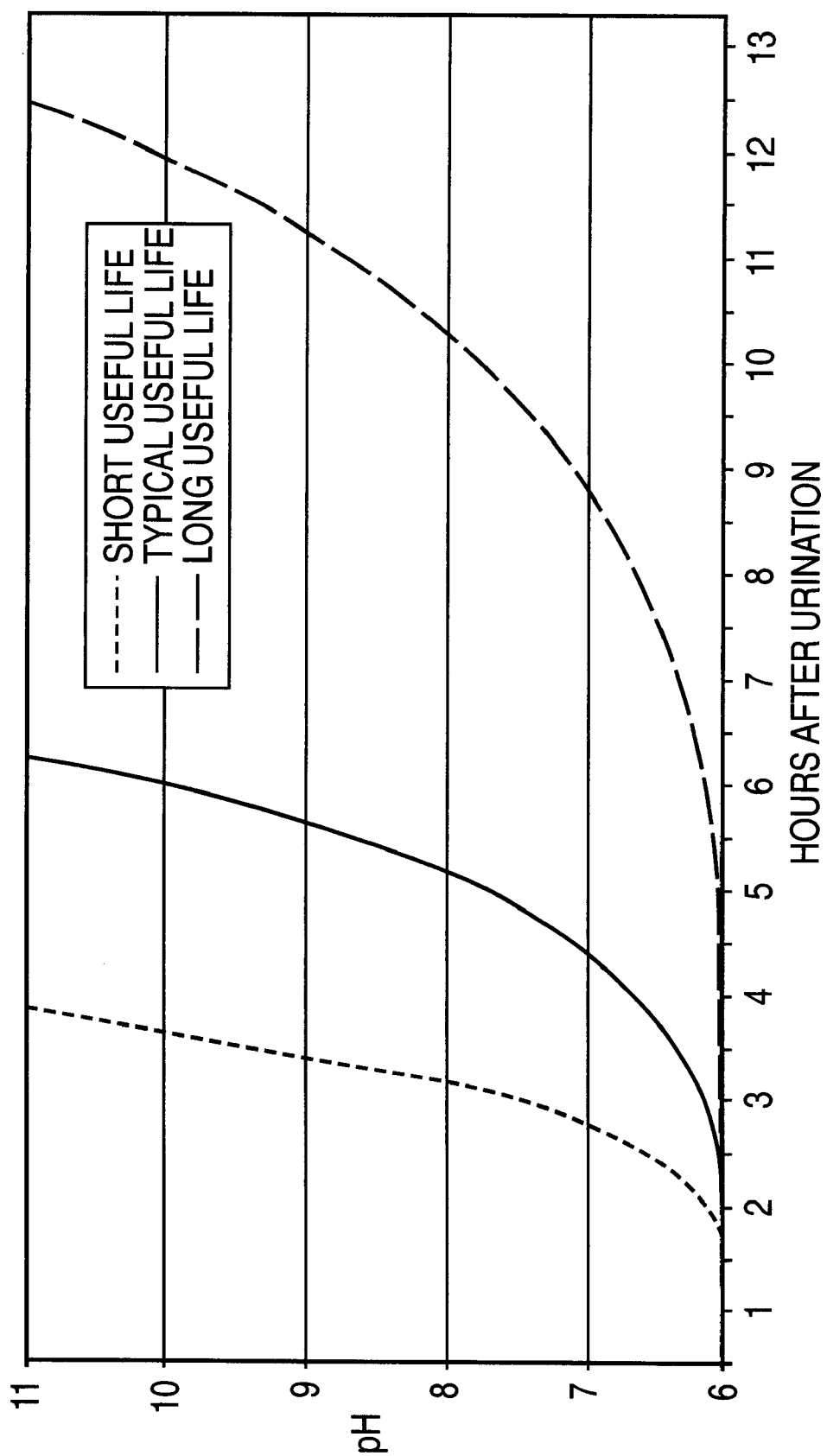
FIG. 1 is a graph illustrating the relationship of pH in the diaper to time from initial urination.

Personal absorbent products become unsafe to the user when harmful conditions develop in and around the absorbent article. Over time, such harmful conditions can result in wearers' prolonged exposure to alkalinity and microbial toxins. The longer a diaper is worn, the faster ammonia is formed and the faster pH rises. A fast-rising pH triggers rapid proliferation of some microbes, such as urea positive bacteria and pathogenic gut bacteria which produce proteolytic enzymes. In a leak-resistant diaper, excrement may be added continually and decomposes while the toxic by-products of decomposition have no means of escaping the diaper's closed system.

The current invention addresses this problem by providing caregivers a real-time indication of the alkalinity level in the diaper, as measured by the pH, and, subsequently, whether the diaper has developed harmful conditions or will do so imminently.

What is invented is a method and apparatus for predicting the remaining safe life of diapers and other absorbent articles (such as incontinence garments, wound dressings, catamenial products such as sanitary napkins, dressings, and the like), and warning that the time to change the absorbent article is imminent. The term "safe life," as used herein, means the period of time during which the absorbent article does no harm to the wearer.

In one embodiment of the present invention, a chemically reactive means is incorporated into the diaper that will provide ongoing visual indication of the pH of the environment in and around the diaper. By continuous measurement and indication of the pH at various sites in the diaper, the presently claimed invention predicts the failure of the diaper at those sites. Since conditions at each location worsen continuously over time, it is not possible to make useful predictions on the basis of a single observation. Therefore, this must be a kinetics-based measurement.

Urine enters a diaper at a normal pH of about 6.2, ranging up to about 7.2, depending on the pathological condition of the wearer. The urine-urea undergoes deamination by urease-producing bacteria. With urease as the catalyst, ammonia begins to be formed in the urine according to the formula $CO(NH_2)_2 + H_2O \rightarrow CO_2 + 2NH_3$. Ammonia is continuously formed, and the pH of the environment rises. At about pH 7.5 to 8.5 the following reaction commences: $CO(NH_2)_2 + 2H_2O \rightarrow HCO_3^- + NH_4^+ + NH_3$. The factors that determine the rate of ammonia production and pH rise include temperature, available urea, the biomass of the inoculum of urea-positive organisms present, the wetness and pH of the skin, the volume of urine, and the mass, moisture content and bacteria content of the feces. Long-lasting diapers first begin to be toxic when the urine pH reaches about 6.5 to 7. Generally, this level is reached between about 4 and about 5 hours after the wearer urinates, although it may be reached as early as hour 2.5 or as late as hour 9.

The second major period of toxicity occurs when the urine pH is between about 7.5 to 8.5. Generally, this period begins about 5 hours after the wearer urinates, although it may begin as early as about 3 hours or as late as about 10 hours after urination. At this pH level, ammonia gas begins to enter the diaper's absorbent core.

The third major period of toxicity begins when the urine pH reaches about 8.5. Generally, pH 8.5 is reached at about 5.5 hours after the initial urination, although it may begin as early as about 3.25 hours or as late as about 11 hours after the initial urination. During this period, the concentration of ammonia gas will begin to permeate back through the membrane topsheet around the absorbent core. The rapidly rising pH increases the activity of many proteolytic enzymes; the free ammonia contacts skin and, if any, feces. Ammonium hydroxide forms and may reach concentrations as high as 1.5%. Caustic irritation and burning of skin and other membranes will continue with increasing severity until the diaper is removed.

Because of the many factors determining the rate at which a diaper becomes unsafe to the wearer, the useful life span of a diaper can vary greatly, as shown in FIG. 1. Thus, it is not possible to set forth a precise schedule at which each stage of toxicity will be reached and how much time remains before a diaper must be changed to avoid damage to the wearer and/or the leak or rupture of the diaper. In order to provide caregivers information they can use to make a timely change, it is very useful to keep them informed about the ongoing shifts in pH to increasingly alkaline values leading up to unsafe conditions. In a preferred embodiment, there will be one or more pH indicators that change color during each of the periods of toxicity described above incorporated into the diaper and visible to the caregiver.

Such a series of indications is useful in maintaining healthy skin for all users, and particularly when the wearer is sensitive to small shifts in alkalinity, such as when the wearer has a pre-existing condition where stratum corneum is compromised. The remaining time before the diaper becomes unsafe depends in part on the condition of the skin of the wearer. To prevent exacerbation of pre-existing skin damage, wearers with compromised skin should have a diaper change as soon as possible after an indication that the pH has reached the first toxicity level (preferably within 30 minutes) and before the appearance of the second indicator color change indicates that the second major period of toxicity has been reached. Wearers with healthy skin should have a diaper change as soon as possible after the second indicator color change to prevent skin irritation. If the third stage of toxicity is reached, the diaper must be changed immediately. If the diaper is not changed until an indication that the third toxic stage has been reached, severe skin irritation and leaks or ruptures of the diaper are likely to occur.

Attendants can readily learn from experience how to "read" the color change indicators with a sense of timing for the color changes that will occur if the diaper is not changed. That is, attendants can interpret the color change timing to know that the diaper will become unsafe in a predictable period of time. The time sequence for the ammonia formation and pH rise in superabsorbent, leak-proofed diapers includes so many variables that the timing and stages for the indicator signals must be fairly broad-ranged; however, precise timing is not required since the indicator signals are predictive, not simply recordations.

Figure 2:
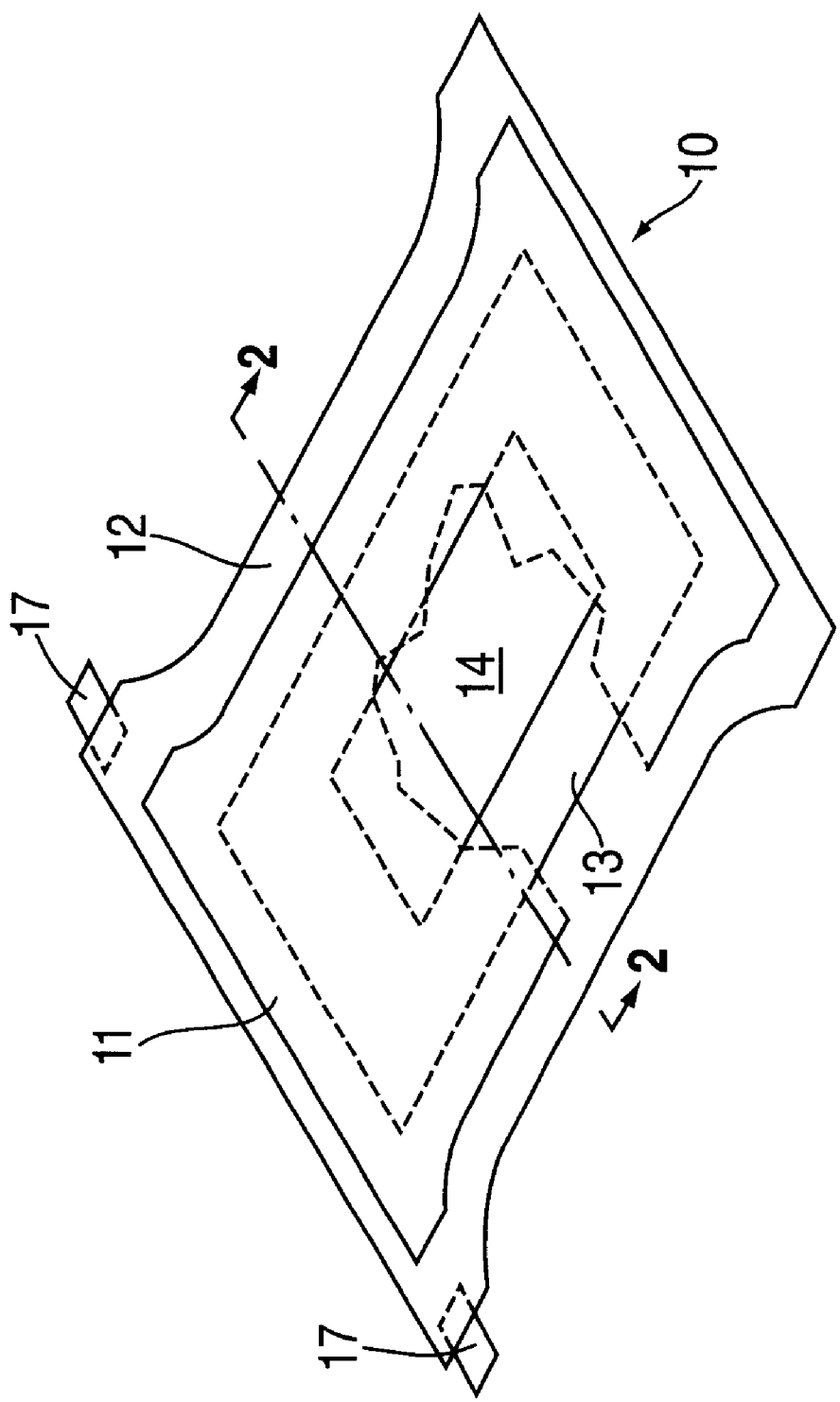
FIG. 2 is a perspective view, shown partially in cutaway, of the interior of a diaper incorporating a chemically reactive indicator means.

Referring now in detail to the drawings herein, like parts being designated by like reference numerals throughout, there is illustrated in FIG. 2, a perspective view of a diaper that is designated generally by reference number 10.

FIG. 2 illustrates a liquid-permeable topsheet 11 in facing superimposed relation with the inner surface of a liquid-impermeable coversheet 12, and an absorbent core 13, which is located between topsheet 11 and coversheet 12. When placed on the wearer, it is the topsheet side that will be in contact with the wearer's skin. A receptor 14 is located between topsheet 11 and absorbent core 13. The receptor is contacted by urine, which is then transported to a chemically reactive means (not shown). The chemically reactive means will involve a sensor that responds to a change in pH and indicates this response visually by a color change. Thus, the chemically reactive means can be considered a combination sensor-indicator. Alternatively, there may be multiple receptors in place of the receptor 14. The placement of receptors may vary from one type or size of diaper to another.

The absorbent core should be capable of absorbing or retaining urine and other body exudates. The absorbent core is preferably compressible, conformable, and non-irritating to the skin. It may include any of a wide variety of liquid-absorbent materials commonly used in absorbent articles, including comminuted wood pulp, meltblown polymers including coform, chemically stiffened, modified or cross-linked cellulosic fibers, synthetic fibers such as crimped polyester fibers, tissue including tissue wraps and tissue laminates, absorbent foams, absorbent sponges, super-absorbent polymers, absorbent gelling materials, or any equivalent material, or any combination or mixture of these materials.

FIG. 3, a cross-sectional view of the diaper of FIG. 2, illustrates the receptor 14 located between topsheet 11 and absorbent core 13, a conductor 15 located between receptor 14, and a sensor-indicator 16 located between the absorbent core 13 and the coversheet 12. The receptor 14 is contacted by urine, which is taken by the conductor 15 to the sensor-indicator 16, which is visible through the coversheet 12. The coversheet 12 may be transparent or may contain a transparent section 17, through which the sensor-indicator 16 is visible to the caregiver.

FIG. 4, a perspective view of the exterior of the diaper of FIG. 2, illustrates the sensor-indicator 16, which is visible through the topsheet 12, if transparent, or through a transparent section thereof.

One or more receptors, as shown in FIG. 2, provide measurements from various locations because the flow of urine and gases in and around the diaper causes variations in pH at different zones in and around the article. Urine enters the diaper, passes through the topsheet, and is wicked and channeled through the absorbent core for storage at the farthest remove from the location where feces tend to collect. Receptors, such as fibrous materials and other wicking agents well known to those skilled in the art, are placed in the absorbent core to transport urine to the sensor-indicator.

The receptors shown in FIGS. 2 and 3 are contacted by urine and pass the urine along a conductor 15 as shown in FIG. 3. The conductor may be a fibrous strip or any porous material that can conduct the urine. The urine is conducted along 15 to a sensor-indicator 16, located on the interior of the coversheet 12, as shown in FIG. 4, which is visible to users and caregivers.

FIG. 5 illustrates a perspective view of another diaper that includes the sensor-indicator system of the present invention, designated generally by reference number 20. There is a liquid-permeable topsheet 21 in facing superimposed relation with the inner surface of a liquid-impermeable coversheet 22, and an absorbent core 23, which is located between topsheet 21 and coversheet 22. An insertion channel 28 is formed as a pocket between the coversheet 22 and the topsheet 21 that allows for insertion of a stick 29 adjacent to absorbent core 23. On the stick 29 there is a sensor-indicator 26. The stick 29 is inserted into the insertion channel 28 such that the sensor-indicator 26 contacts the urine in the absorbent core 23. Alternatively there may be multiple sensor-indicators 26 on the stick 29 or elsewhere on the diaper. In one embodiment, the stick 29 may be removed so that the color change on sensor-indicator 26 may be viewed; alternatively the coversheet 22 over all or a portion of insertion channel 28 may be transparent so that color changes on the sensor-indicator 26 may be viewed without removing the stick 29.

FIG. 6, a cross-sectional view of the diaper of FIG. 5, illustrates the insertion channel 28 located between topsheet 21 and absorbent core 23. The insertion channel 28 contains the stick 29, which is adjacent to absorbent core 23, so that the pH changes of the urine in absorbent core 23 can be detected and visibly indicated by the sensor-indicator(s) (not shown in this view) on the stick 29.

Urine is discharged into the diaper at up to 15–20 ml/second, but is only taken up by the absorbent core at a rate of about 8 ml/second. The urine that is not immediately taken up puddles against the skin and contacts feces, if any, before it is absorbed. As previously noted, the pH of this urine rises faster than urine at any other location in the diaper, because feces contain urea-cleaving bacteria that speed deamination.

Initially, the take-up rate of the absorbent core increases once it is wetted. Subsequently, as the absorbent core becomes increasingly saturated, the take-up rate slows and the volume of urine puddling against the skin and feces increases. The urine that puddles against the skin and feces contacts the area of the diaper that form leg openings. Accordingly, for greater accuracy in predicting the remaining safe life of the diaper, additional receptors may also be placed in this area.

The sensor-indicator is coated and/or impregnated with chemicals from the group that respond to pH changes in the range. When the urine contacts the sensor-indicator, chemical reactions are initiated which result in series of color changes indicative of the urine pH. Many color change pH indicators are commercially available for the pH range of 6.0 to 10+.

A preferred sensor-indicator contains an indicator that changes color at in the pH range between about 6.5 and about 7.5, preferably between about 6.6 to about 7.3, and then changes color again at a pH of about 7.5 to about 10 or more. Preferably there is a third indicator color change at a pH between about 8.5 and about 10, preferably between about 8.5 and about 9.0. This may be achieved by using a mixture of several different dyes, selected such that the mixture provides distinct color changes at the required resolution (e.g., every 0.5 pH unit). A simple example of such a mixture is one containing phenol red and thymol blue. With such a mixture, a progressive increase in pH from below 6.6 to over 9.6 might be indicated by color changes from yellow to orange to purple.

Alternatively, multiple indicators, each changing color over a different pH range may be used. For example, a strip containing a series of small, discrete indicators that change color, separated by buffers and hydrophobic dividers, may be used. Such strips are commercially available, such as BAKER-pHIX™ narrows range Universal pH Indicator Sticks. These indicators contain four distinct stages that change color over ranges 6.0–7.7 and 7.5–9.5.

Other means of visibly indicating pH means may be used, such as alpha numerics, i.e. "A, B, C," or graphics, i.e. a green to yellow to red array of indicators like a traffic light or a bullseye.

Color change indicator materials for ammonia and pH are well known and widely commercially available. They are commonly manufactured as film coatings or emulsions comprising various cellulosic and/or polymeric components including gels, adhesives and other materials in a matrix. Ammonia indicators, such as azoic dyes that react with ammonia and cause a color-change, are commercially available from Tennessee Eastman Company and others. Azoic dyes can be buffered and combined with other dyes to provide a broad spectrum of hues of varying intensities.

The following table lists commercially available pH indicator materials that are specific to the stages of pH levels described herein.

| pH Range | pH Indicators | Color Change |
|---|---|---|
| 6.2–7.6 | Bromothymol blue | yellow to blue |
| 6.4–8.0 | Phenol red | yellow to red |
| 6.6–8.6 | m-Nitrophenol | colorless to yellow |
| 6.8–8.0 | Neutral Red | bluish-red to orange-yellow |
| 7.0–8.0 | Quinoline blue | colorless to violet |
| 7.2–8.8 | Cresol red | yellow to red |
| 7.3–8.7 | 1-Naphtholphthalein | colorless to blue-green |
| 7.6–9.0 | Metacresol purple | yellow to purple |
| 8.0–9.6 | Thymol blue | yellow to blue |
| 8.0–9.6 | p-Xylenol blue | yellow to blue |
| 8.2–9.8 | Phenolphthalein | colorless to purple |

-continued

| pH Range | pH Indicators | Color Change |
|---|---|---|
| 8.2–9.8 | o-Cresolphthalein | colorless to red/violet |
| 9.3–10.5 | Thymolphthalein | colorless to blue |
| 10.0–12.1 | Alizarin yellow GG | colorless to yellow |
| 10.1–11.1 | Nile blue | blue to red |
| 9.8–11.0 | α-Naphtholbenzein | yellow to blue |
| 10.2–12.0 | Alizarin Yellow | yellow to red |

One of skill in the art can select appropriate indicators from the list (or any other commercially available indicators) suitable for use in the present invention.

The dyes can be immobilized on an absorbent material such as paper, or to a small absorbent pad or fibrous strips. The paper can be placed in the diaper in such a way that it comes in contact with urine and is visible outside the diaper. Various treated papers and tapes that change color in the above pH ranges can be bonded to the diaper interior and extended to the outer surface; such materials include universal and intermediate indicators sold by Hydrion Papers, EM Corp., and others.

The paper, pad or strip may be fixed to the inner surface of cover sheet 12 at manufacture and viewed through transparent window 16. Alternatively, the pad may be attached to a removable plastic strip and viewed by withdrawing the strip periodically, or the dyes may be applied directly to the absorbent article or to a small absorbent pad or fibrous strip that can be inserted in the diaper at a suitable location.

In another embodiment of the present invention, the pH indicating means may be an electrochemical indicator.

Figure 7:
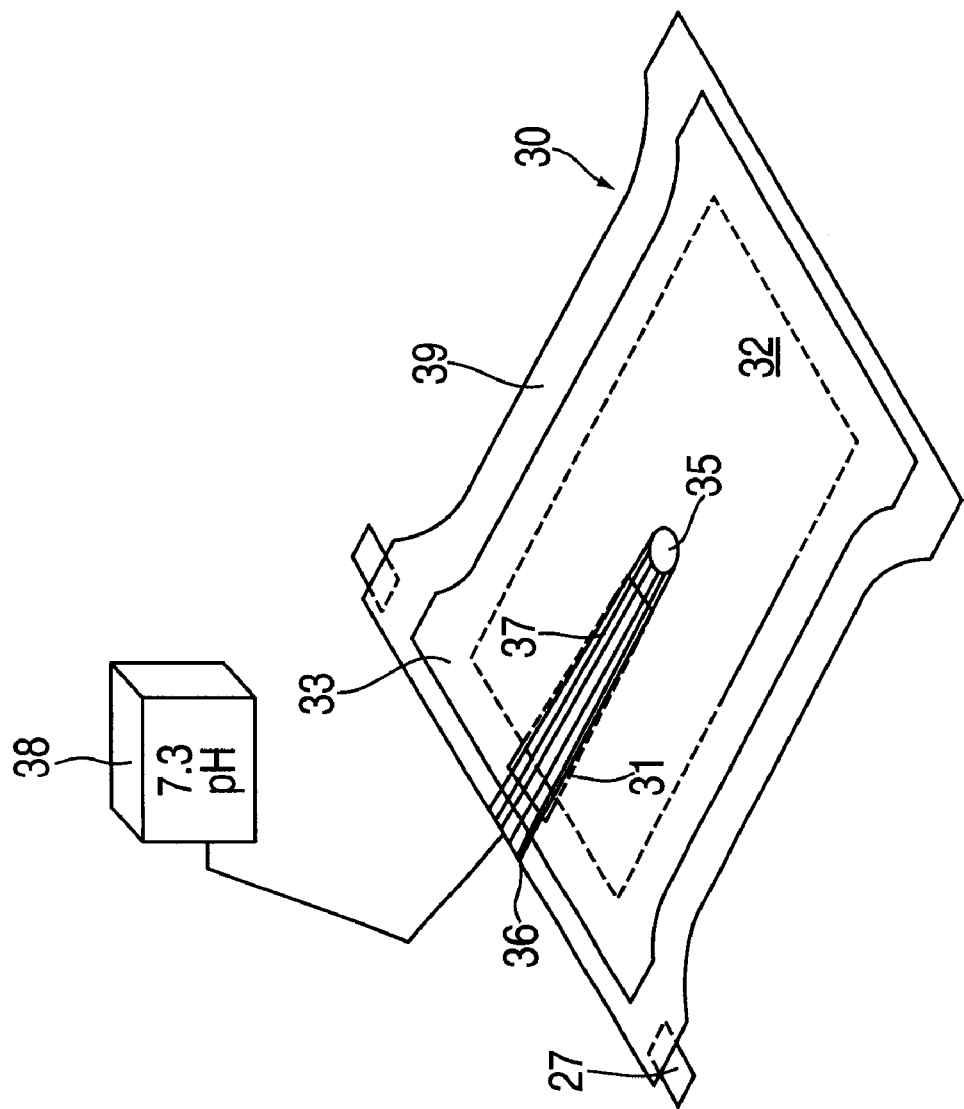
FIG. 7 is a perspective view of the interior of a diaper incorporating an electrochemical indicator means.

FIG. 7 illustrates a diaper 30 having an electrochemical indicator means in accordance with one embodiment of the present invention. Diaper 30 also includes an absorbent core 32, which is provided sandwiched between a liquid-permeable topsheet 33 and a liquid-impermeable coversheet 39. Electrochemical indicator 32 may be inserted into diaper 30 through an insertion channel 31. Insertion channel 31 is located primarily between absorbent core 32 and topsheet 33.

Electrochemical indicator 32 includes an electrochemical cell 35 coupled to a terminator 36 by a number of conductive lines 37. Electrochemical cell 35 is preferably a combination of a pH sensor and a reference electrode. The pH sensor preferably provides an electrical signal that contains information about conditions within diaper 30, such as an electric potential that depends on pH. Electrochemical cell 35 should preferably be able to reside in an absorbent article without its performance being compromised.

Suitable sensors for electrochemical indicator 32 include glass or polymer membrane electrodes, metal-metal oxide electrodes, metal oxide electrodes, and ion-sensitive field effect transistors (ISFETs). Suitable metal-metal oxide electrodes include antimony/antimony oxide, aluminum/aluminum oxide, and iridium/iridium oxide. Iridium-iridium oxide electrodes, for example, are insensitive to most ions such as copper, sodium, and potassium, and are not affected by oxygen, carbon dioxide, ammonia, and hydrogen sulfide. They can be stored dry over a long period. Suitable metal oxide electrodes include, but are not limited to, iridium oxide and osmium oxide.

Combination glass membrane electrodes are commercially available. These combination electrodes contain an internal reference electrode together with the pH sensor.

Rugged reference electrodes containing silver/silver chloride and copper/copper sulfate couples are commercially available.

Solid state reference electrodes have been described in the technical literature. A suitable electrochemical sensor for use in absorbent products, such as diapers, might be comprised of a metal-metal oxide pH electrode and a solid state reference electrode.

An electrochemical potential from the pH sensor is measured with respect to the potential of the reference electrode. The potential difference may be displayed on a simple meter 38 which is coupled to terminator 36. Meter 38 is preferably configured to indicate the pH within diaper 30 and provide information as to when diaper 30 should be changed. In a preferred embodiment, meter 38 is portable and preferably small enough to clip on to the outside of the absorbent article.

Figure 8:
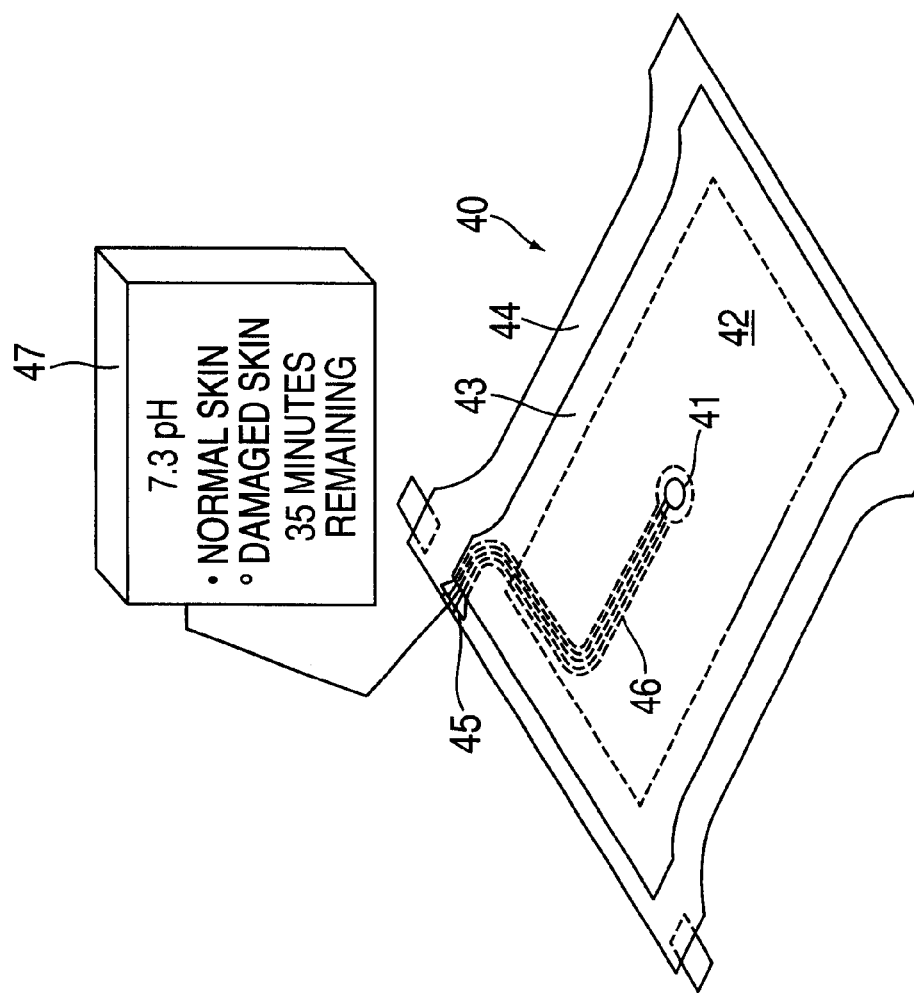
FIG. 8 is a perspective view of the interior of a diaper incorporating an electrochemical indicator means.

FIG. 8 illustrates another diaper, designated generally by reference number 40, having an electrochemical indicator means in accordance with one embodiment of the present invention. Diaper 40 is similar to diaper 30 referred to in FIG. 7, however the electrochemical indicator is designed not to be removed from diaper 40. Diaper 40 also includes an absorbent core 42, which is provided sandwiched between a liquid-permeable topsheet 43 and a liquid-impermeable coversheet 44.

The electrochemical indicator of FIG. 8 includes an electrochemical cell 41 coupled to a terminator 45 by a number of conductive lines 46. Electrochemical cell 41 is preferably a combination of a pH sensor and a reference electrode operating in the same fashion as electrochemical cell 35 of FIG. 7. Electrochemical cell 41 is preferably located between absorbent core 42 and topsheet 43. Terminator 45 is preferably located on the periphery of diaper 40 so that it may be coupled to a pathogenic prediction meter 47.

Pathogenic prediction unit 47 is a more sophisticated version of meter 38 of FIG. 7. Pathogenic prediction unit 47 incorporates an analog-to-digital converter, memory (dynamic random access memory, or DRAM), and a microprocessor. The voltage signal from the sensor may thus be recorded by converting it into a digital form, which is stored in the memory. The stored voltage data represents the pH as a function of time. The pH-time dependence may be displayed visually by pathogenic prediction unit 47 or electronically analyzed by the microprocessor using a curve-fitting procedure as described below.

Figure 9:
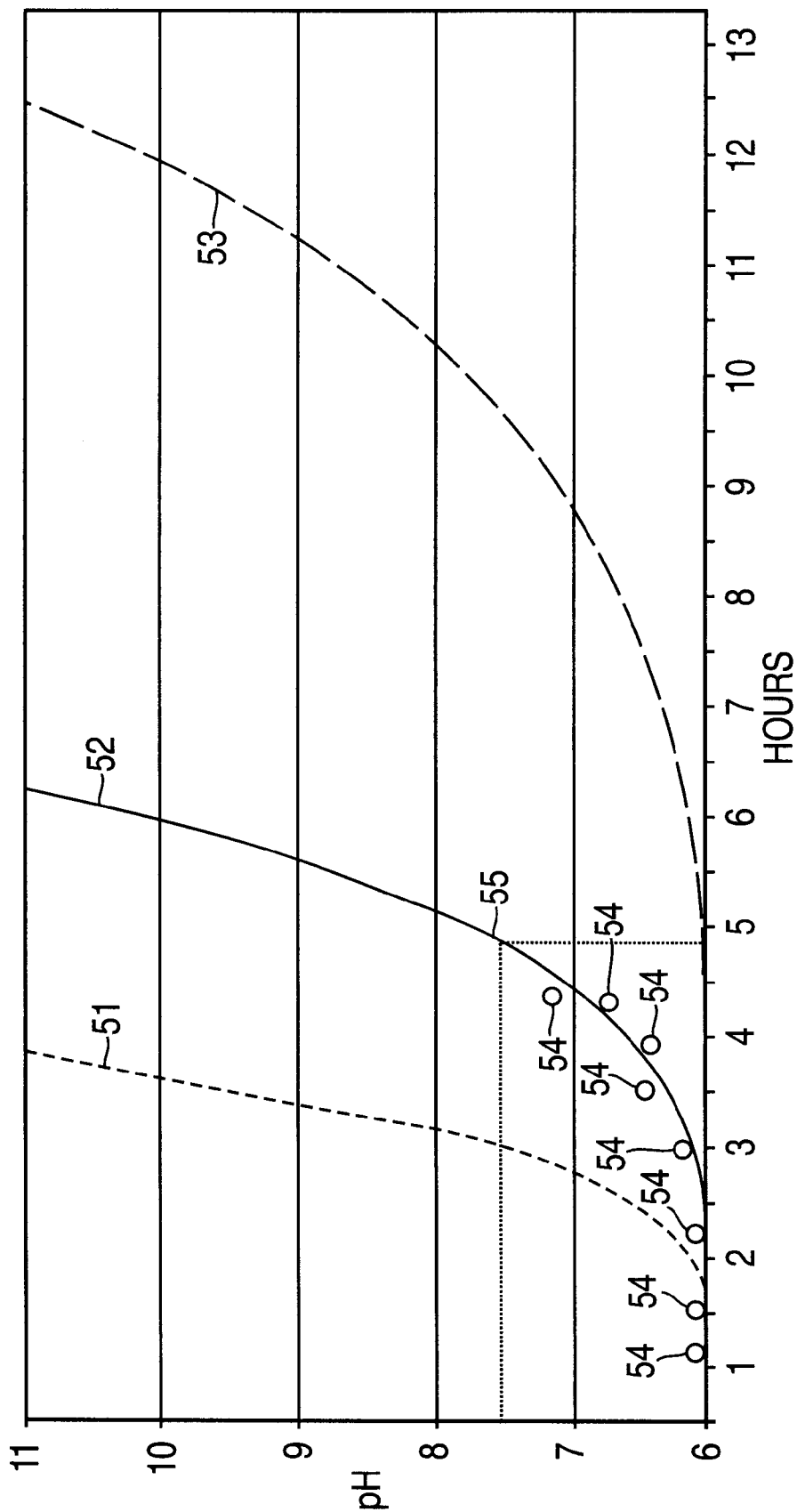
FIG. 9 is a diagram of a series of curves that may be used to predict pH kinetic variability in diapers.

FIG. 9 is a diagram of a series of curves 51, 52, and 53 that may be used to predict to pH kinetic variability in diapers in accordance with one embodiment of the present invention. Although more curves may be used, for ease of illustration, only three curves are shown. Each curve represents a pH-time equation that may be used to predict how long it might take to reach a preselected pH value. As the pH sensor monitors pH levels in a diaper at regular intervals, it will generate a series of data points 54 that are compared to curves that are stored in memory, such as curves 51, 52, and 53. As soon as the best curve fit is identified, which in this example is curve 55, the microprocessor will locate the point on that curve where pH reaches a dangerous level. The dangerous pH level in this case is indicated by point 55 at a pH of 7.5.

The dangerous pH level may be adjusted according to the skin condition of the diaper wearer. The microprocessor may then compute the length of time it should take to reach a dangerous pH level based on the curve. Because the process of measuring pH and curve matching continues throughout the time in which the diaper is worn, different curves may be selected adjusting to the new data points. However, changes in the projected time it should take to reach a dangerous pH would be buffered, so as to gradually change, and not be overly responsive to statistically inconsistent changes. The length of time may be displayed on a pathogenic prediction unit 55 along with the current pH of the diaper.

In another preferred embodiment of the present invention, the relays and signals of the pH sensor are calibrated to provide warning signals that the pH levels and gas concentrations in the diaper will become pathogenic at a predicted time, preferably 10 to 30 minutes beforehand. The electric signal generated by the sensor may result in a visual indicator, which changes color based on the pH. The color change signals should be clear, well-paced, and easily visible on the diaper exterior. The electric signal generated by the sensor may also result in an audible signal that is loud enough to warn the wearer or a caregiver that the diaper must be changed.

By providing these signals, this improved diaper permits caregivers to be more efficient, and provides wearers with greater comfort and safety. Used properly, a diaper in accordance with the present invention provides protection against dermatological conditions caused by extended exposure to alkaline environments, and more rapid healing of pre-existing dermatological conditions. Thus, the invention is believed to provide urgently needed utilitarian benefits, as well as useful social benefits.

While this invention has been described with respect to an absorbent article in the form of a disposable or reusable diaper, it will be appreciated that the invention could be applied to other absorbent products such as but not limited to, diaper insert pads, feminine hygiene products, incontinence products, bedding, bandages, and other such articles.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A diaper comprising:
   a liquid impervious outer layer having opposite side edges and opposed end edges connecting the side edges, said outer layer defining a shape and dimensions of the diaper, the diaper having a crotch portion adapted to engage a crotch of a wearer to capture and retain waste material when the diaper is folded medially and worn engaging a waist area and stomach area of the wearer;
   a first layer adapted to contact skin of the wearer;
   an electrochemical indicator for measuring pH of an interior environment of said diaper, said electrochemical indicator being located between said first layer and said liquid impervious outer layer, wherein said electrochemical indicator is operable to measure a series of pH levels over time and generate a series of electrical signals based on said series of pH levels;
   a pathological prediction unit operable to receive said series of electric signals, wherein said pathological prediction unit performs curve matching on said series of pH levels and determines a time at which said interior environment of said diaper is predicted to reach a set of conditions where pathogenic microbes or pathological environments are present, which will deleteriously affect the wearer, based on a selected curve.

2. A diaper as recited in claim 1, wherein the electrochemical indicator includes an electrochemical cell having a pH sensor and a reference electrode.

3. A diaper as recited in claim 2, wherein the electrochemical indicator further includes a terminator coupled to the electrochemical cell by a number of conductive lines, wherein said terminator is coupled to the pathogenic prediction unit.

4. A diaper as recited in claim 3, wherein said pathogenic prediction unit displays a current pH of the interior environment of the diaper.

5. A diaper as recited in claim 4, wheren said pathological prediction unit displays the time at which the interior environment of the diaper is predicted to reach a set of conditions where pathogenic microbes or pathological environments are present, which will deleteriously affect the wearer.

6. A diaper as recited in claims 4, wherein said pathological prediction unit displays an amount of time remaining until the interior environment of the diaper is predicted to reach a set of conditions where pathogenic microbes or pathological environments are present, which will deleteriously affect the wearer.

7. A method of predicting remaining safe life of a diaper comprising the steps of:
   measuring a series of pH levels of an interior environment of said diaper;
   matching a selected curve to said series of pH levels by comparing said series of pH levels with a series of curves; and
   predicting a time at which said interior environment of said diaper is predicted to reach a set of conditions where pathogenic microbes or pathological environments are present, which will deleteriously affect the wearer, based on said selected curve.

8. A method of predicting remaining safe life of a diaper as recited in claim 7, further comprising the step of indicating a time remaining until the predicted time at which the interior environment of the diaper is predicted to reach a set of conditions where pathogenic microbes or pathological environments deleteriously affect the wearer.

9. A method of predicting remaining safe life of a diaper as recited in claim 7, further comprising indicating a time at which the diaper should be changed based on the predicted time at which the interior environment of the diaper is predicted to reach a set of conditions where pathogenic microbe or pathological environments deleteriously affect the wearer.

10. A method of predicting the remaining safe life of a diaper as recited in claim 9, wherein said indicating a time at which the diaper should be changed includes a visual indicator.

11. A method of predicting the remaining safe life of a diaper as recited in claim 10, wherein said visual indicator includes a color change.

12. A method of predicting the remaining safe life of a diaper as recited in claim 9, wherein the indicating a time at which a diaper should be changed includes an audible signal.

13. A diaper comprising:
   a liquid impervious outer layer having opposite side edges and opposed end edges connecting the side edges, said outer layer defining a shape and dimensions of the diaper, the diaper having a crotch portion adapted to engage a crotch of a wearer to capture and retain waste material when the diaper is folded medially and worn engaging a waist area and stomach area of the wearer;
   a first layer adapted to contact skin of a wearer;
   an electrochemical indicator for measuring pH of an interior environment of said diaper, said electrochemical indicator being located between said first layer and said liquid impervious outer layer, wherein said electrochemical indicator is operable to measure a series of pH levels over time and generate a series of electrical signals based on said series of pH levels;
   a pathological prediction unit operable to receive said series of electric signals, wherein said pathological prediction unit analyzes said series of pH levels and determines a time at which said interior environment of said diaper is predicted to reach a set of conditions where pathogenic microbes or pathological environments are present, which will deleteriously affect the wearer.

* * * * *